(12) United States Patent
Edie et al.

(10) Patent No.: US 7,794,501 B2
(45) Date of Patent: Sep. 14, 2010

(54) EXPANDABLE INTERVERTEBRAL SPACERS AND METHODS OF USE

(75) Inventors: Jason A Edie, Memphis, TN (US); Lloyd Guyton Bowers Cooper, Birmingham, AL (US); Don Byron Walker, II, Muscle Shoals, AL (US)

(73) Assignee: Wasaw Orthopedic, Inc., Warsaw, IN (US)

( * ) Notice: Subject to any disclaimer, the term of this patent is extended or adjusted under 35 U.S.C. 154(b) by 954 days.

(21) Appl. No.: 11/412,671

(22) Filed: Apr. 27, 2006

(65) Prior Publication Data

US 2007/0255413 A1    Nov. 1, 2007

(51) Int. Cl.
*A61F 2/44*    (2006.01)

(52) U.S. Cl. ............... 623/17.12; 623/17.15; 623/17.16

(58) Field of Classification Search .................. 606/277, 606/290; 623/17.11, 17.12, 17.15, 17.16
See application file for complete search history.

(56) References Cited

U.S. PATENT DOCUMENTS

| | | | |
|---|---|---|---|
| 4,553,273 A | 11/1985 | Wu | |
| 4,554,914 A | 11/1985 | Kapp et al. | |
| 4,657,550 A | 4/1987 | Daher | |
| 4,820,305 A | 4/1989 | Harms et al. | |
| 4,932,975 A | 6/1990 | Main et al. | |
| 5,002,576 A | 3/1991 | Fuhrmann et al. | |
| 5,026,373 A | 6/1991 | Ray et al. | |
| 5,062,850 A | 11/1991 | MacMillan et al. | |
| 5,236,460 A * | 8/1993 | Barber | 623/17.15 |
| 5,336,223 A | 8/1994 | Rogers | |
| 5,360,430 A | 11/1994 | Lin | |
| 5,397,364 A | 3/1995 | Kozak et al. | |
| 5,480,442 A | 1/1996 | Bertagnoli | |
| 5,522,899 A | 6/1996 | Michelson | |
| 5,571,190 A | 11/1996 | Ulrich et al. | |
| 5,571,192 A | 11/1996 | Schönhöffer | |
| 5,658,335 A | 8/1997 | Allen | |
| 5,702,451 A | 12/1997 | Biedermann et al. | |
| 5,702,453 A | 12/1997 | Rabbe et al. | |
| 5,702,455 A | 12/1997 | Saggar | |
| 5,723,013 A | 3/1998 | Jeanson et al. | |
| 5,725,528 A | 3/1998 | Errico et al. | |
| 5,776,197 A | 7/1998 | Rabbe et al. | |
| 5,776,198 A | 7/1998 | Rabbe et al. | |
| 5,989,290 A | 11/1999 | Biedermann et al. | |
| 6,015,436 A | 1/2000 | Schonhoffer | |
| 6,086,613 A | 7/2000 | Camino et al. | |

(Continued)

FOREIGN PATENT DOCUMENTS

DE    10052008 C1    8/2002

(Continued)

OTHER PUBLICATIONS

"International Search Report," International Application No. PCT/US2007/065910, Sep. 19, 2007, European Patent Office, Rijswijk, Netherlands.

*Primary Examiner*—Eduardo C Robert
*Assistant Examiner*—Elana B Fisher

(57) ABSTRACT

An intervertebral spacer is inserted between vertebral members in a compact configuration and expanded post-insertion to contact the adjacent vertebral members. The intervertebral spacer comprises a first member and a second member movable with respect to the first member between retracted and extended positions.

29 Claims, 7 Drawing Sheets

U.S. PATENT DOCUMENTS

| | | | |
|---|---|---|---|
| 6,156,038 | A | 12/2000 | Zucherman et al. |
| 6,176,881 | B1 | 1/2001 | Schär et al. |
| 6,190,413 | B1 | 2/2001 | Sutcliffe |
| 6,190,414 | B1 | 2/2001 | Young et al. |
| 6,193,755 | B1 | 2/2001 | Metz-Stavenhagen et al. |
| 6,193,756 | B1 | 2/2001 | Studer et al. |
| 6,200,348 | B1 | 3/2001 | Biedermann et al. |
| 6,296,665 | B1 | 10/2001 | Strnad et al. |
| 6,299,644 | B1 | 10/2001 | Vanderschot |
| 6,344,057 | B1 | 2/2002 | Rabbe et al. |
| 6,352,556 | B1 | 3/2002 | Kretschmer et al. |
| 6,375,681 | B1 | 4/2002 | Truscott |
| 6,375,682 | B1 | 4/2002 | Fleischmann et al. |
| 6,375,683 | B1 | 4/2002 | Crozet et al. |
| 6,395,032 | B1 | 5/2002 | Gauchet |
| 6,395,034 | B1 | 5/2002 | Suddaby |
| 6,409,766 | B1 | 6/2002 | Brett |
| 6,447,547 | B1 | 9/2002 | Michelson |
| 6,454,806 | B1 | 9/2002 | Cohen et al. |
| 6,520,991 | B2 | 2/2003 | Huene |
| 6,524,341 | B2 | 2/2003 | Läng et al. |
| 6,610,090 | B1 | 8/2003 | Böhm et al. |
| 6,616,695 | B1 * | 9/2003 | Crozet et al. ............. 623/17.11 |
| 6,645,249 | B2 | 11/2003 | Ralph et al. |
| 6,648,917 | B2 | 11/2003 | Gerbec et al. |
| 6,652,074 | B2 | 11/2003 | Silverbrook |
| 6,660,038 | B2 | 12/2003 | Boyer, II et al. |
| 6,719,796 | B2 | 4/2004 | Cohen et al. |
| 6,723,126 | B1 | 4/2004 | Berry |
| 6,752,832 | B2 | 6/2004 | Neumann |
| 6,758,862 | B2 | 7/2004 | Berry et al. |
| 6,776,798 | B2 | 8/2004 | Camino et al. |
| 6,783,547 | B2 | 8/2004 | Castro |
| 6,793,678 | B2 | 9/2004 | Hawkins |
| 6,808,538 | B2 | 10/2004 | Paponneau |
| 6,835,207 | B2 | 12/2004 | Zacouto et al. |
| 6,852,129 | B2 | 2/2005 | Gerbec et al. |
| 6,863,673 | B2 | 3/2005 | Gerbec et. al. |
| 6,866,682 | B1 | 3/2005 | An et al. |
| 6,893,465 | B2 | 5/2005 | Huang |
| 6,902,579 | B2 | 6/2005 | Harms et al. |
| 6,908,485 | B2 | 6/2005 | Crozet et al. |
| 2003/0187438 | A1 * | 10/2003 | Assaker et al. ................. 606/61 |
| 2003/0191531 | A1 | 10/2003 | Berry et al. |
| 2003/0199980 | A1 | 10/2003 | Siedler |
| 2004/0049271 | A1 | 3/2004 | Biedermann et al. |
| 2004/0073314 | A1 | 4/2004 | White et al. |
| 2004/0172129 | A1 | 9/2004 | Schafer et al. |
| 2004/0181283 | A1 | 9/2004 | Boyer, II et al. |
| 2004/0186569 | A1 | 9/2004 | Berry |
| 2005/0004572 | A1 | 1/2005 | Biedermann et al. |
| 2005/0060036 | A1 | 3/2005 | Schultz et al. |
| 2005/0090898 | A1 * | 4/2005 | Berry et al. ............... 623/17.11 |
| 2005/0113921 | A1 | 5/2005 | An et al. |
| 2005/0209698 | A1 | 9/2005 | Gordon et al. |
| 2005/0273169 | A1 | 12/2005 | Purcell |
| 2006/0241770 | A1 * | 10/2006 | Rhoda et al. .............. 623/17.15 |

FOREIGN PATENT DOCUMENTS

| | | |
|---|---|---|
| EP | 1 080 703 A2 | 8/2000 |
| EP | 1 188 424 A1 | 8/2001 |
| WO | WO 03/073964 A1 | 9/2003 |
| WO | WO 03/096937 A1 | 11/2003 |
| WO | WO 2004/026157 A2 | 4/2004 |
| WO | 2004/0443304 A | 5/2004 |
| WO | WO 2004/096103 A1 | 11/2004 |
| WO | WO 2004/100837 A1 | 11/2004 |
| WO | 2005/041818 A | 5/2005 |
| WO | WO 2005/055887 A2 | 6/2005 |

* cited by examiner

EXPANDABLE INTERVERTEBRAL SPACERS AND METHODS OF USE

BACKGROUND

The present application is directed to devices and methods for stabilizing vertebral members, and more particularly, to intervertebral implants and methods of use for replacing an intervertebral disc, vertebral member, or combination of both to distract and/or stabilize the spine.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve. Intervertebral discs are positioned between the vertebral members and permit flexion, extension, lateral bending, and rotation.

Various conditions may lead to damage of the intervertebral discs and/or the vertebral members. The damage may result from a variety of causes including a specific event such as trauma, a degenerative condition, a tumor, or infection. Damage to the intervertebral discs and vertebral members can lead to pain, neurological deficit, and/or loss of motion.

Various procedures include replacing the entirety or a section of a vertebral member, the entirety or a section of an intervertebral disc, or both. One or more replacement implants may be inserted to replace the damaged vertebral members and/or discs. The implants reduce or eliminate the pain and neurological deficit, and increase the range of motion.

SUMMARY

The present application is directed to intervertebral spacers inserted between vertebral members in a compact configuration and expanded post-insertion to contact the adjacent vertebral members. The intervertebral spacers may comprise a first member and a second member movable with respect to the first member between retracted and extended positions. During insertion, the second member may be placed in a retracted position relative to the first member. A fluid cylinder or air cylinder accessible to the surgeon post-insertion may be actuated to expand the intervertebral spacer to the desired height. The intervertebral spacer may be used to replace an intervertebral disc, vertebra, or combination of both.

In one embodiment, the first member includes a first cylinder formed therein. The second member includes a second cylinder that is sized and configured to insert into the first cylinder. The first and second cylinders define an expansion chamber. A fluid valve is provided for introducing fluid into said expansion chamber to expand said intervertebral spacer. A secondary locking mechanism locks the superior member at the adjusted height. The secondary locking mechanism comprises a slot defining first and second clamping portions and a force generating member to apply a clamping force to said first and second clamping sections.

DETAILED DESCRIPTION

Figure 1:
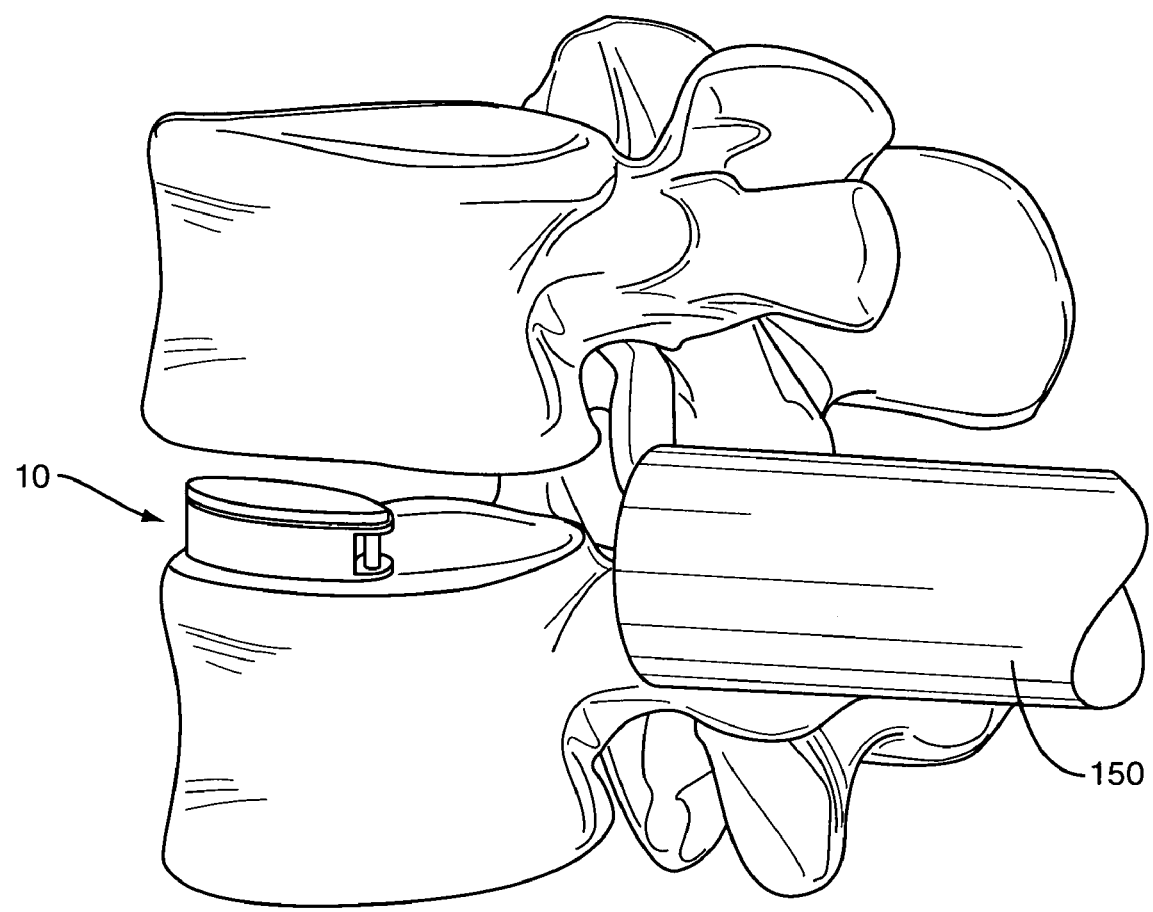
FIG. 1 is a perspective view of an exemplary intervertebral spacer in a retracted position disposed between two vertebral members.
Figure 2:
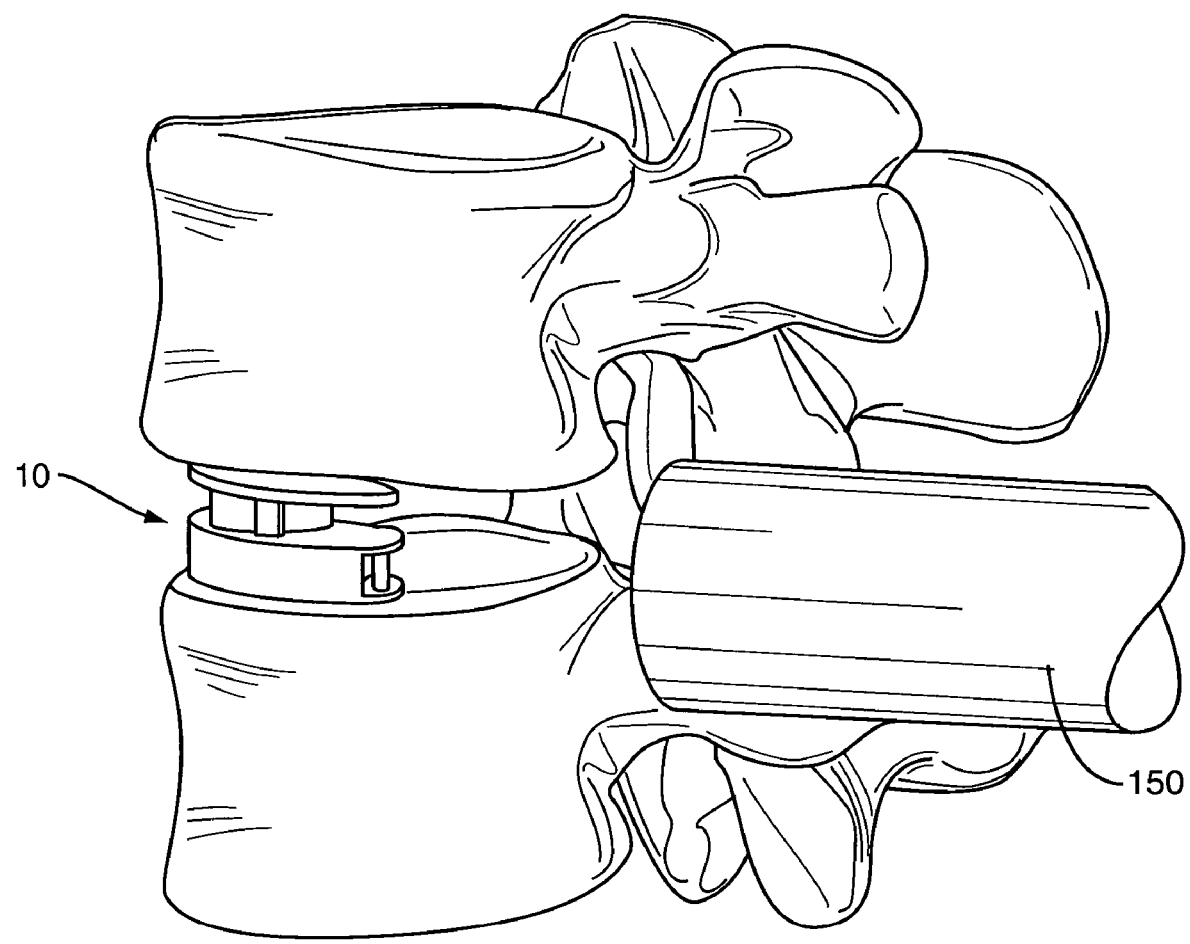
FIG. 2 is a perspective view of an exemplary intervertebral spacer in an extended position disposed between two vertebral members.

The present application relates to implants for replacing an intervertebral disc, vertebral member, or combination of both, and to methods of inserting the same. The implant comprises an intervertebral spacer 10 that can be inserted between vertebral bodies in a compact configuration as shown in FIG. 1 and subsequently expanded to contact the adjacent vertebral bodies as shown in FIG. 2.

Figure 3:
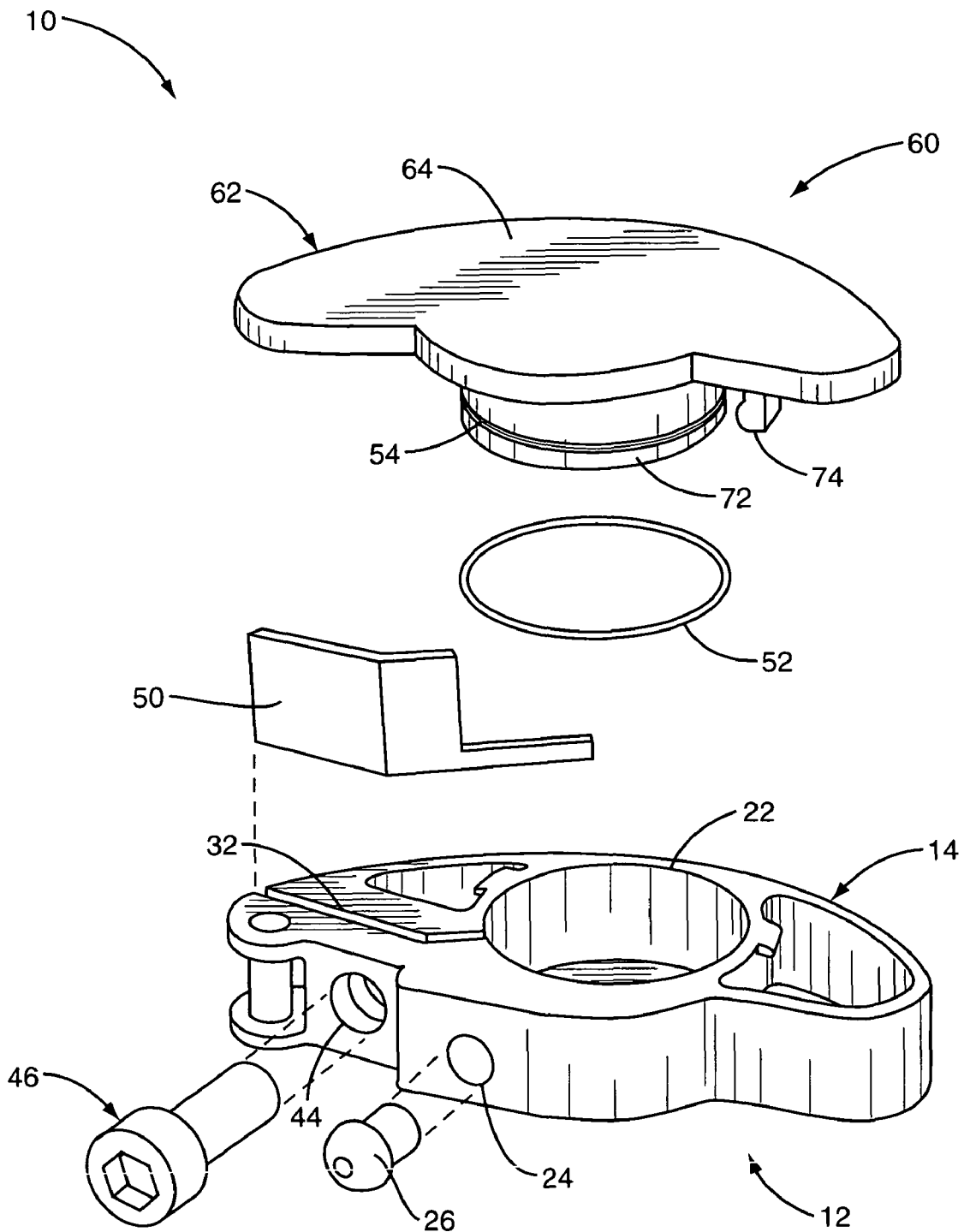
FIG. 3 is an exploded perspective view of an exemplary intervertebral spacer.
Figure 4:
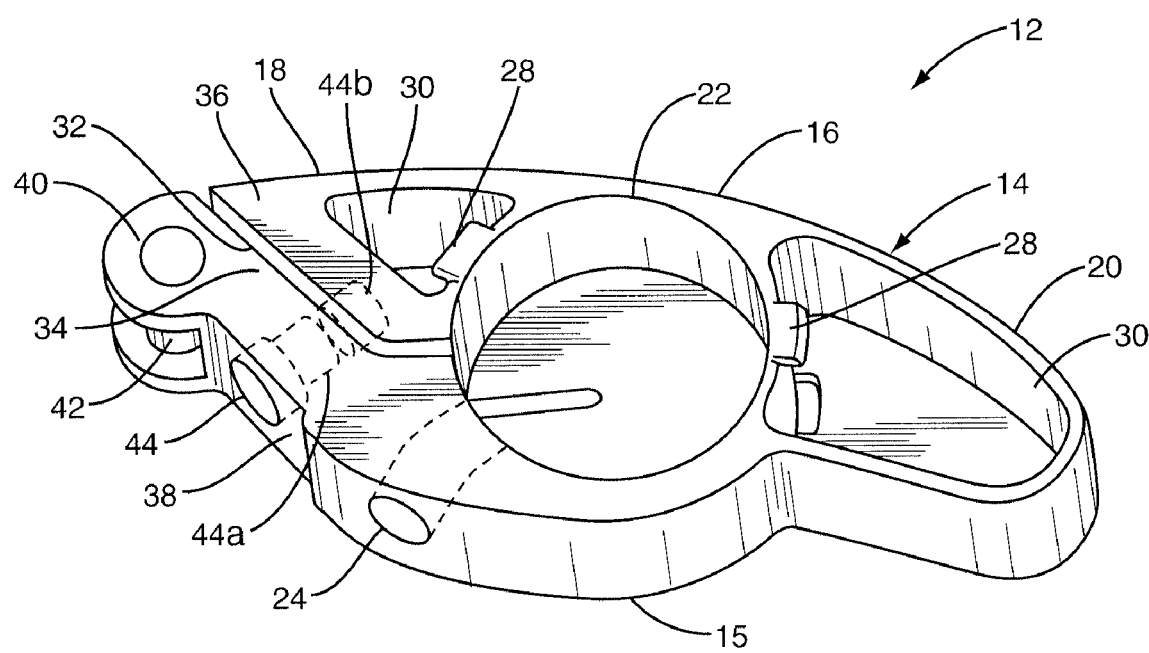
FIG. 4 is a perspective view of an inferior member for an exemplary intervertebral spacer.
Figure 5:
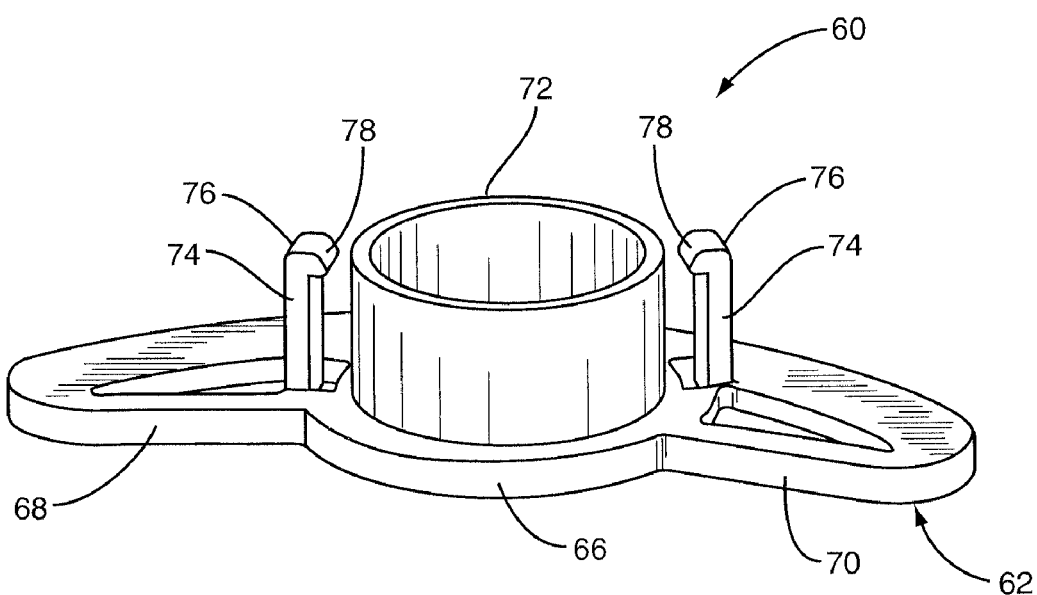
FIG. 5 is a perspective view of a superior member for an exemplary intervertebral spacer.

FIGS. 3-5 illustrates one exemplary embodiment of the intervertebral spacer 10. The intervertebral spacer 10 comprises an inferior member 12 and a superior member 60 movable with respect to the inferior member 12 from a retracted position to an extended position. As will be described in more detail below, the inferior member 12 includes a first cylinder 22, and the superior member 60 includes a second cylinder 72 that is insertable into the first cylinder 22. The cylinders 22 and 72 together define a expansion chamber. When fluid is introduced into the expansion chamber, the superior member 60 is urged away from the inferior member 12. While cylinders 22 and 72 are shown having a circular cross-section, those skilled in the art will appreciate that the cylinders 22 and 72 can have other shapes, such as square, rectangular, oval, kidney-shape, etc.

FIG. 4 illustrates details of one embodiment of the inferior member 12. The inferior member 12 comprises a body 14 including a bottom surface 15 that contacts an adjacent vertebral body. The bottom surface 15 can be textured to grip the vertebral body. For example, teeth, ridges, or grooves can be formed in the bottom surface 15 to improve gripping capability. The body 14 has an oblong configuration including a central section 16 and wing sections 18 and 20. Cylinder 22 is formed in the central section 16. A fluid port 24 is formed in the central section 16 for introducing fluid into the expansion chamber formed by cylinders 22 and 72. A one-way valve 26 (FIG. 3) is disposed in the fluid port 24 that allows introduction of fluid, such as a saline solution, into the expansion chamber, and prevents fluid from exiting the expansion chamber. One or more cavities 30 may be formed in the wing sections 18 and 20 to reduce weight and material requirements.

A slot 32 is formed in the wing section 18. Slot 32 divides the wing section 18 into first and second clamping portions 34 and 36, respectively, and intersects both the wall and bottom of the cylinder 22. A compressible seal 50 is disposed within the slot 32 to prevent fluid from leaking from the expansion chamber. Clamping portion 34 includes a recessed surface 38. A pair of spaced-apart ears 40 project outward from the recessed surface 38 for mounting a pin 42. The ends of the pin 42 are firmly secured in openings formed in the ears 40. Any suitable techniques for securing the pin 42 can be used. A screw hole 44 extends inward from the recessed surface 38 to receive a locking screw 46. The screw hole 44 crosses the slot 32 such that the screw hole 44 is divided into two portions 44a, 44b. Portion 44b of the screw hole 44 is threaded. When the locking screw 46 is tightened, the clamping portions 34 and 36 are pulled together, causing a slight contraction of the cylinder 22. As will be hereinafter described, this clamping arrangement functions as a locking mechanism to lock the superior member 60 firmly in place once proper height adjustment has been made.

The superior member 60, shown in FIG. 5, comprises a plate 62 having a top surface 64 that engages an adjacent vertebral body. The top surface 64 can be textured to grip the vertebral body. For example, small teeth, ridges, or grooves can be formed in the top surface 64 to improve gripping capability. The top plate 62 is shaped to generally correspond to the shape of the inferior member 12. The top plate 62 includes a central section 66 and wing sections 68 and 70. A cylinder 72 extends from the bottom surface of the top plate 62. Cylinder 72 is sized to fit within the cylinder 22 in the inferior member 12. In one embodiment, the interior dimension of the cylinder 22 and exterior diameter of the cylinder 22 are sized to close tolerances such that a seal is formed between the interior wall of cylinder 22 and outer surface of cylinder 72. However, those skilled in the art will appreciate that a ring seal 52 may be used to form a fluid tight seal between cylinders 22 and 72. An annular groove 54 may also be formed in the outer surface of the cylinder 72 to position the seal 52.

A mechanism can be provided to prevent the inferior member 12 and superior member 60 from separating. In one embodiment, a pair of resilient fingers 74 extends downward from the bottom surface of the top plate 62 of superior member 60. The enlarged ends 76 of the resilient fingers 74 are configured to engage the locking tabs 28 on the inferior member 12. When the superior member 60 is assembled with the inferior member 12, the ends of the locking fingers 74 contact the locking tabs 28. Camming surfaces 78 on the enlarged ends 76 of the locking fingers 74 cause the resilient fingers 74 to flex outward and pass over the locking tabs 28. Once the enlarged ends 76 have passed over the locking tabs 28, the resilient fingers 74 return to their original position, thereby preventing separation of the superior member 60. Thus, the resilient fingers 74 and locking tabs 28 cooperate to retain the superior member 60 in place.

Figure 6:
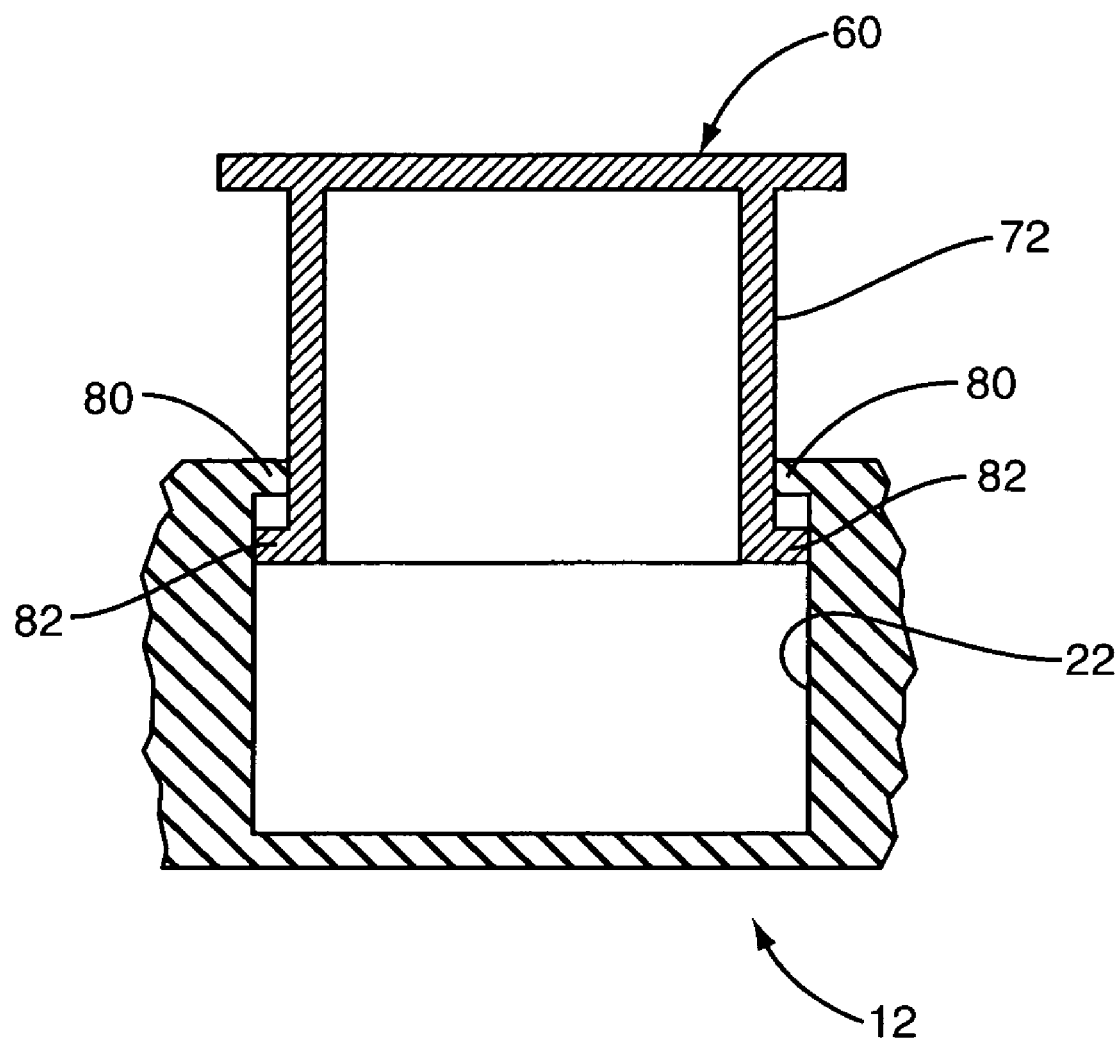
FIG. 6 is a detail view of one exemplary intervertebral spacer.

FIG. 6 illustrates an alternate method of preventing separation of the inferior member 12 and superior member 60. In this embodiment, an inwardly projecting lip 80 is formed at the top end of cylinder 22 and an outwardly projecting lip 82 is formed at the bottom end of cylinder 72. In this embodiment, the superior member 60 can be assembled with the inferior member 12 by dipping the superior member 60 in a cold liquid, such as liquid nitrogen, to shrink the superior member 60. When the superior member 60 shrinks, the lip 82 on cylinder 72 will pass through the lip 80 on cylinder 22. The superior member 60 will then expand to its original size as it returns to ambient temperatures.

The inferior member 12 and superior member 60 can be made of any suitable material, such as PEEK. The bottom of the inferior member 12 and/or top late 62 of the superior member 60 could be porous to allow the in-growth of bone. An embedded biologic coating, such as hydroxia appetite (HA), BMP, or calcium phosphate could be used to promote bone in-growth. The contact surfaces of the inferior and superior members 12 and 72 could also be textured to grip the adjacent vertebral bodies.

In use, the superior member 60 is assembled to the inferior member 12 and placed in a compact configuration with the superior member 60 in a retracted position relative to the inferior member 12 as shown in FIG. 1. The intervertebral spacer 10, in a compact configuration, is inserted through a cannula 150 into an intervertebral space between two vertebral bodies (FIG. 1). Those skilled in the art will appreciate that the intervertebral spacer 10 can replace one or more disks and/or vertebral bodies. After the insertion of the intervertebral spacer 10, fluid or compressed air is introduced into the expansion chamber to cause the superior member 60 to extend away from the inferior member 12 as shown in FIG. 2. The superior member 60 is raised until the contact surfaces of the inferior and superior members 12 and 60 are engaged with the adjacent vertebral bodies. Once the height of the intervertebral spacer 10 is properly adjusted, the locking screw 24 is tightened to lock the superior member 60 in a fixed position relative to the inferior member 12. Tightening the locking screw 46 causes the cylinder 22 of the inferior member 12 to contract and clamp against the exterior surface of cylinder 22. Thus, the cylinder 22 itself functions as a clamp that will lock the inferior and superior members 12, 60 in position, even in the event that fluid leaks from the expansion chamber.

Figure 7:
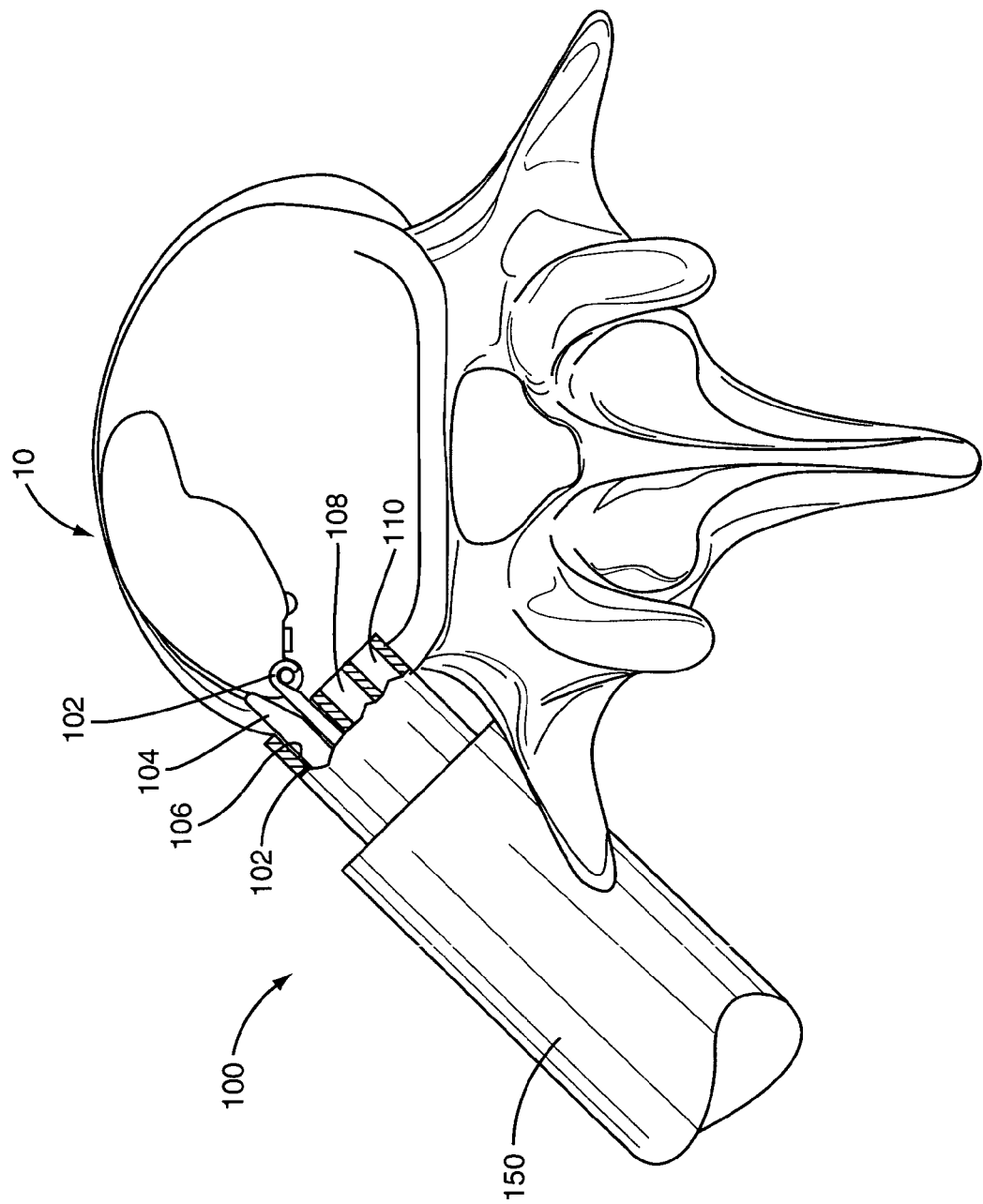
FIGS. 7 and 8 illustrate an exemplary method of inserting the intervertebral spacer.
Figure 8:
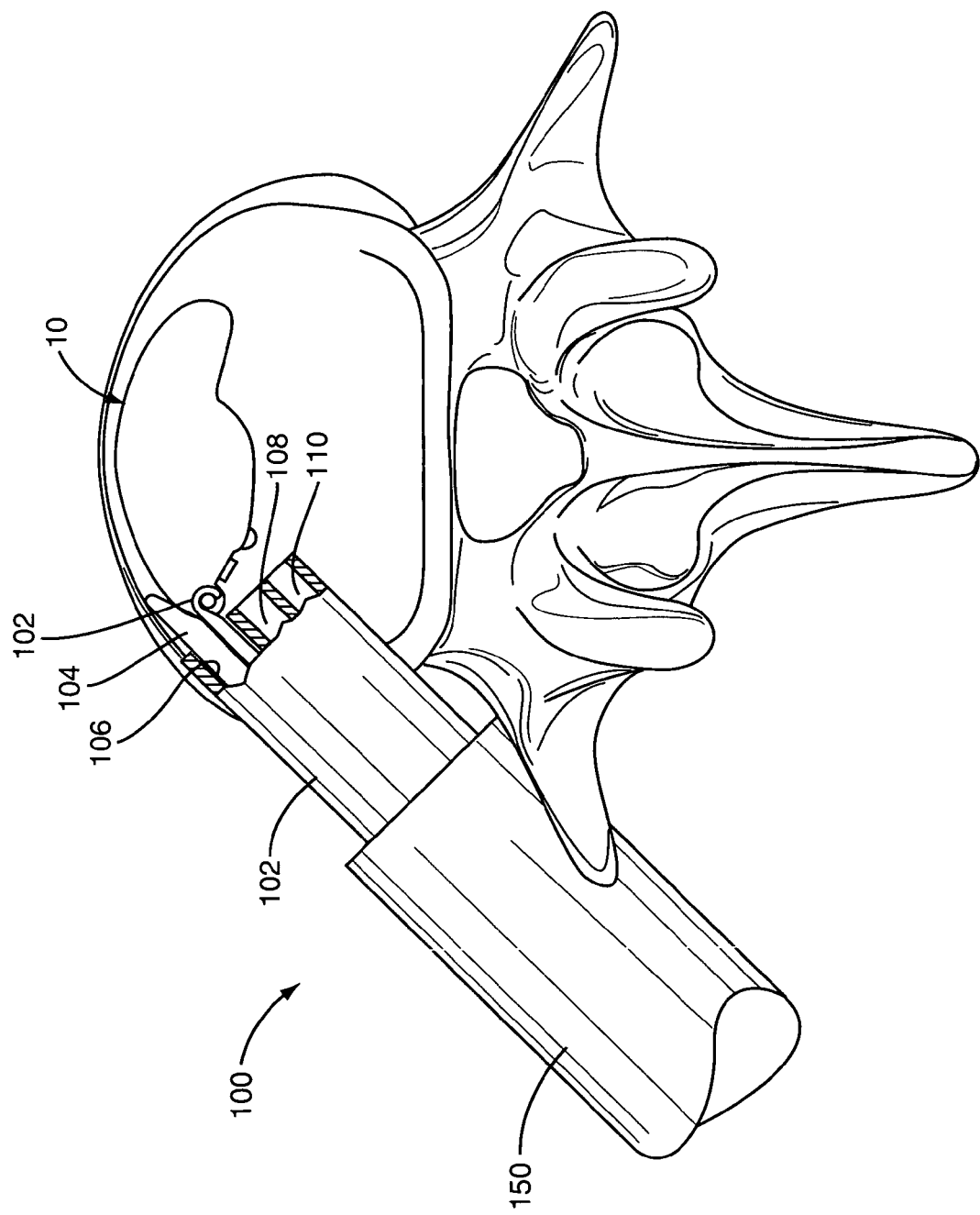

FIGS. 7 and 8 illustrate an exemplary insertion tool 100 to insert the intervertebral spacer 10. The insertion tool 100 includes an elongate housing 102 having three lumens 106, 108, and 110 formed therein. Access to the intervertebral space is gained through a cannula 150 inserted into the body. FIGS. 7 and 8 illustrate the distal end of the cannula 150 and insertion tool 100. The insertion tool 100 includes a hook member 102 that engages pin 42 on the intervertebral spacer 10. As the intervertebral spacer 10 is advanced through the cannula 150, the intervertebral spacer 10 initially assumes the position shown in FIG. 7. When the intervertebral spacer 10 exits from the end of the cannula 150, a push rod 104 is used to rotate the intervertebral spacer 10 into the proper angular position.

The hook member 102 and push rod 104 pass through the first lumen 106. The second lumen 108 aligns with the locking screw 46. The third lumen 110 aligns with the fluid valve 26. After the intervertebral spacer 10 is properly positioned, a fluid delivery line can be inserted through lumen 110 and engaged with the fluid valve 26 to deliver fluid into the expansion chamber to expand the intervertebral spacer 10. A tool can then be inserted through the middle lumen 108 to tighten the locking screw 42.

The embodiments described above include member 60 being a superior member and member 12 being inferior. In another embodiment, the orientation of these members 60, 12 may be interchanged with member 60 functioning as an inferior member and member 12 functioning as a superior member.

One embodiment includes accessing the spine from a postero-lateral approach. Other applications contemplate other approaches, including posterior, anterior, antero-lateral and lateral approaches to the spine, and accessing other regions of the spine, including the cervical, thoracic, lumbar and/or sacral portions of the spine.

The term "distal" is generally defined as in the direction of the patient, or away from a user of a device. Conversely, "proximal" generally means away from the patient, or toward the user. Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. An intervertebral spacer comprising:
   a first member including a first contact surface to contact an adjacent vertebral body and including a first cylinder formed therein;
   a second member including a second contact surface and including a second cylinder that is insertable into the first cylinder, said first and second cylinders defining an expansion chamber;
   a valve for introducing fluid or compressed gas into said expansion chamber to expand said intervertebral spacer;
   a slot formed in said first member intersecting the first cylinder, said slot defining first and second clamping portions on opposing sides of said slot;
   a force generating member to apply a clamping force to said first and second clamping portions that is transmitted through the first and second clamping portions to the first cylinder to cause the first cylinder to contract around the second cylinder; and
   a compressible seal in said slot to contain said fluid or compressed gas in said expansion chamber.

2. The intervertebral spacer of claim 1 wherein the force generating member comprises a screw that is tightened to generate the clamping force.

3. The intervertebral spacer of claim 1 further comprising a retaining mechanism to prevent the first and second cylinders from separating.

4. The intervertebral spacer of claim 3 wherein the retaining mechanism comprises one or more resilient fingers formed on either the first or second member for engaging one or more tabs on the other member.

5. The intervertebral spacer of claim 3 wherein the retaining mechanism comprises an inwardly projecting element formed at the upper end of the first cylinder and an outwardly projecting element formed at the bottom end of the second cylinder arranged to contact said inwardly projecting element.

6. The intervertebral spacer of claim 1 further comprising a seal between an interior wall of said first cylinder and an exterior wall of the second cylinder to contain said fluid or compressed gas in said expansion chamber.

7. The intervertebral spacer of claim 1 further comprising a tool-engaging member for engagement by an insertion tool.

8. The intervertebral spacer of claim 7 wherein said tool-engaging member is configured to permit rotation of said intervertebral spacer during its insertion between intervertebral bodies.

9. The intervertebral spacer of claim 8 wherein the tool-engaging member comprises a pin configured for engagement by a hook on an insertion tool, said hook being rotatable around said pin.

10. The intervertebral spacer of claim 1 wherein at least one of the first and second members includes a portion that is porous to promote in-growth of bone into the intervertebral spacer.

11. The intervertebral spacer of claim 1 wherein at least one of the first and second contact surfaces includes a texture to grip an adjacent intervertebral body.

12. An intervertebral spacer comprising:
    first and second members to contact adjacent vertebral bodies;
    a fluid cylinder connected to said first and second members, said fluid cylinder including a outer cylinder connected to said first member and an inner cylinder connected to said second member; and
    a clamping mechanism on said first member to lock said fluid cylinder in a fixed position, said clamp mechanism configured to cause the outer cylinder to contract and clamp against said inner cylinder;
    the clamping mechanism including a slot formed in said first member intersecting the outer cylinder, said slot defining first and second clamping portions in opposing sides of said slot, said slot extending into a surface of the first member that faces away from a bottom wall of the first member, and a force generating member to apply a clamping force to said first and second clamping portions that is transmitted through the first and second clamping portions to the outer cylinder to cause the outer cylinder to contract around the inner cylinder; and
    a compressible seal in said slot to contain fluid in said fluid cylinder.

13. The intervertebral spacer of claim 12 wherein the force generating member comprises a screw that is tightened to generate a clamping force.

14. The intervertebral spacer of claim 12 further comprising a retaining mechanism to prevent the inner and outer cylinders from separating.

15. The intervertebral spacer of claim 14 wherein the retaining mechanism comprises one or more resilient fingers formed on either the first or second member for engaging one or more tabs on the other member.

16. The intervertebral spacer of claim 14 wherein the retaining mechanism comprises an inwardly projecting element formed at an upper end of the first cylinder and an outwardly projecting element formed at a bottom end of the second cylinder arranged to contact said inwardly projecting element.

17. The intervertebral spacer of claim 12 further comprising a seal between an interior wall of said outer cylinder and an exterior wall of the inner cylinder to contain said fluid in said expansion chamber.

18. The intervertebral spacer of claim 12 further comprising a tool-engaging member for engagement by an insertion tool.

19. The intervertebral spacer of claim 18 wherein said tool-engaging member is configured to permit rotation of said intervertebral spacer during its insertion between intervertebral bodies.

20. The intervertebral spacer of claim 19 wherein the tool-engaging member comprises a pin configured for engagement by a hook on an insertion tool, said hook being rotatable around said pin.

21. The intervertebral spacer of claim 12 wherein at least one of the first and second members includes a portion that is porous to promote in-growth of bone into the intervertebral spacer.

22. The intervertebral spacer of claim 12 wherein at least one of the first and second members includes a texture to grip an adjacent intervertebral body.

23. An intervertebral spacer comprising:
first and second members to contact adjacent vertebral bodies;
a fluid cylinder connected to said first and second members, said fluid cylinder including a outer cylinder connected to said first member and an inner cylinder connected to said second member;
a slot that extends through the first member and the outer cylinder;
a seal positioned in the slot to prevent fluid from leaking from the fluid cylinder; and
a retaining mechanism preventing separation of said first and second members.

24. The intervertebral spacer of claim 23 wherein the retaining mechanism comprises one or more resilient fingers formed on either the first or second member for engaging one or more tabs on the other member.

25. The intervertebral spacer of claim 23 wherein the retaining mechanism comprises an inwardly projecting element formed at an end of the outer cylinder and an outwardly projecting element formed at an end of the inner cylinder arranged to contact said inwardly projecting element.

26. The intervertebral spacer of claim 23 further including a locking mechanism to lock the first and second members in a fixed position relative to one another.

27. The intervertebral spacer of claim 26 wherein the locking mechanism comprises a clamping mechanism.

28. The intervertebral spacer of claim 23 wherein the first member comprises an inferior member and wherein the second member comprises a superior member.

29. The intervertebral spacer of claim 23 wherein the first member comprises a superior member and wherein the second member comprises an inferior member.

* * * * *